(12) United States Patent
Maschke

(10) Patent No.: US 8,126,534 B2
(45) Date of Patent: Feb. 28, 2012

(54) MEDICAL CATHETER AND SYSTEM FOR INSERTING A CATHETER INTO A VESSEL

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1006 days.

(21) Appl. No.: 11/455,264

(22) Filed: Jun. 16, 2006

(65) Prior Publication Data

US 2006/0287595 A1 Dec. 21, 2006

(30) Foreign Application Priority Data

Jun. 16, 2005 (DE) .................. 10 2005 027 951

(51) Int. Cl.
*A61B 5/00* (2006.01)
(52) U.S. Cl. ....... 600/424; 623/1.11; 600/434; 600/435; 600/466; 600/470; 600/478; 606/130
(58) Field of Classification Search .................. 600/407, 600/410, 413, 414, 417, 420, 423, 424, 425, 600/426, 428, 429, 431, 433, 435, 437, 450, 600/459, 462, 466, 467, 469, 470, 471, 473, 600/476, 478, 479, 481, 427, 585, 434; 606/130; 623/1.11
See application file for complete search history.

(56) References Cited

U.S. PATENT DOCUMENTS

| 4,054,881 | A | 10/1977 | Raab |
| 6,233,476 | B1 | 5/2001 | Strommer et al. |
| 6,546,271 | B1 | 4/2003 | Reisfeld |
| 2001/0031919 | A1 | 10/2001 | Strommer et al. |
| 2002/0049375 | A1 | 4/2002 | Strommer et al. |
| 2002/0143392 | A1 * | 10/2002 | Ryan ........................... 623/1.42 |
| 2003/0015037 | A1 * | 1/2003 | Stephens et al. ................ 73/626 |
| 2003/0236443 | A1 * | 12/2003 | Cespedes et al. ............... 600/29 |
| 2005/0020908 | A1 * | 1/2005 | Birkenbach et al. ........... 600/420 |
| 2005/0256398 | A1 * | 11/2005 | Hastings et al. ............... 600/423 |
| 2006/0064009 | A1 * | 3/2006 | Webler et al. .................. 600/434 |
| 2006/0135870 | A1 * | 6/2006 | Webler ........................... 600/431 |

(Continued)

FOREIGN PATENT DOCUMENTS

DE 198 27 460 A1 12/1998

(Continued)

OTHER PUBLICATIONS

Theis, "Die Antennen ausgefahren lassen!", Vdo nachrichten, New York 11.4.03, 2003, p. 1.

(Continued)

*Primary Examiner* — Brian Casler
*Assistant Examiner* — Amanda Lauritzen

(57) ABSTRACT

The invention relates to a medical system for introducing a catheter into a blood vessel of a patient, having a computer and control unit, a means for creating a transparent general view of the position of the vessel, a catheter with a reversible inflatable balloon located in the front area, to the outside of which a stent can be fitted for implanting into the vessel, a position locating system for the catheter with position and location sensors that can determine the position and location of the catheter, the system with at least one OCT (optical coherence tomography) sensor at a catheter end for the close-up area, with at least one IVUS (intravascular ultrasound) imaging sensor at a catheter end for the remote area and the computer and control unit having image processing and image display functions for the image sensors.

17 Claims, 2 Drawing Sheets

U.S. PATENT DOCUMENTS

2009/0234443 A1* 9/2009 Ottma et al. .................. 623/2.11

FOREIGN PATENT DOCUMENTS

| DE | 200 09 204 U1 | 9/2000 |
| DE | 299 24 228 U1 | 8/2002 |
| DE | 103 43 808 A1 | 5/2005 |
| DE | 103 54 496 A1 | 7/2005 |
| DE | 10 2004 001 498 A1 | 8/2005 |
| EP | 0 878 174 A2 | 11/1998 |
| EP | 0 993 804 A1 | 4/2000 |
| JP | 11148897 A | 6/1999 |
| JP | 11151246 A | 6/1999 |
| JP | 11225942 A | 8/1999 |
| JP | 2002526188 A | 8/2002 |
| JP | 2003235986 A | 8/2003 |
| JP | 2005095624 A | 4/2005 |
| WO | WO 02/07601 A2 | 1/2002 |
| WO | 2004110271 A1 | 12/2004 |
| WO | 2005008583 A2 | 1/2005 |

OTHER PUBLICATIONS

Klipstein, "Nanometerstrukturen stempeln", Vdi nachrichten, Dusseldorf 23.5.03, 2003, p. 1.

Schultz, "Nanometer-Chips sind voll im Plan", Vdi nachrichten, Santa Barbara, 1.8.03, 2003, p1.

"Siliziumscheiben fü Nano-Chips", VDI nachrichten, Burghausen 1.8.03, 2003, p.1.

Sietmann, "Klein, kleiner, noch kleiner", Nano-Elektronik, c't 2003, Heft 17, pp. 80-89.

Communication from Japanese Patent Office, Oct. 25, 2011, pp. 1-9.

* cited by examiner

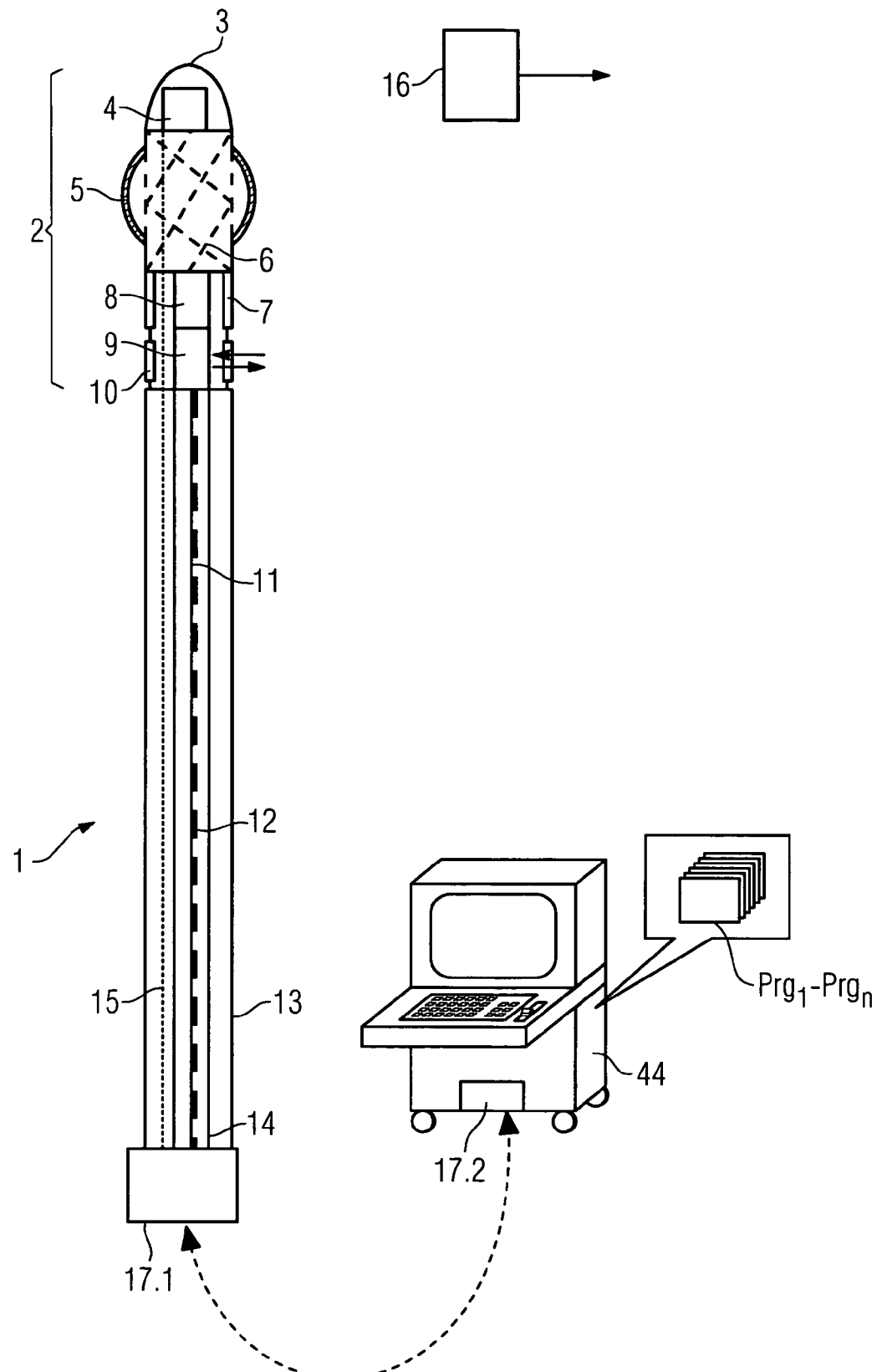

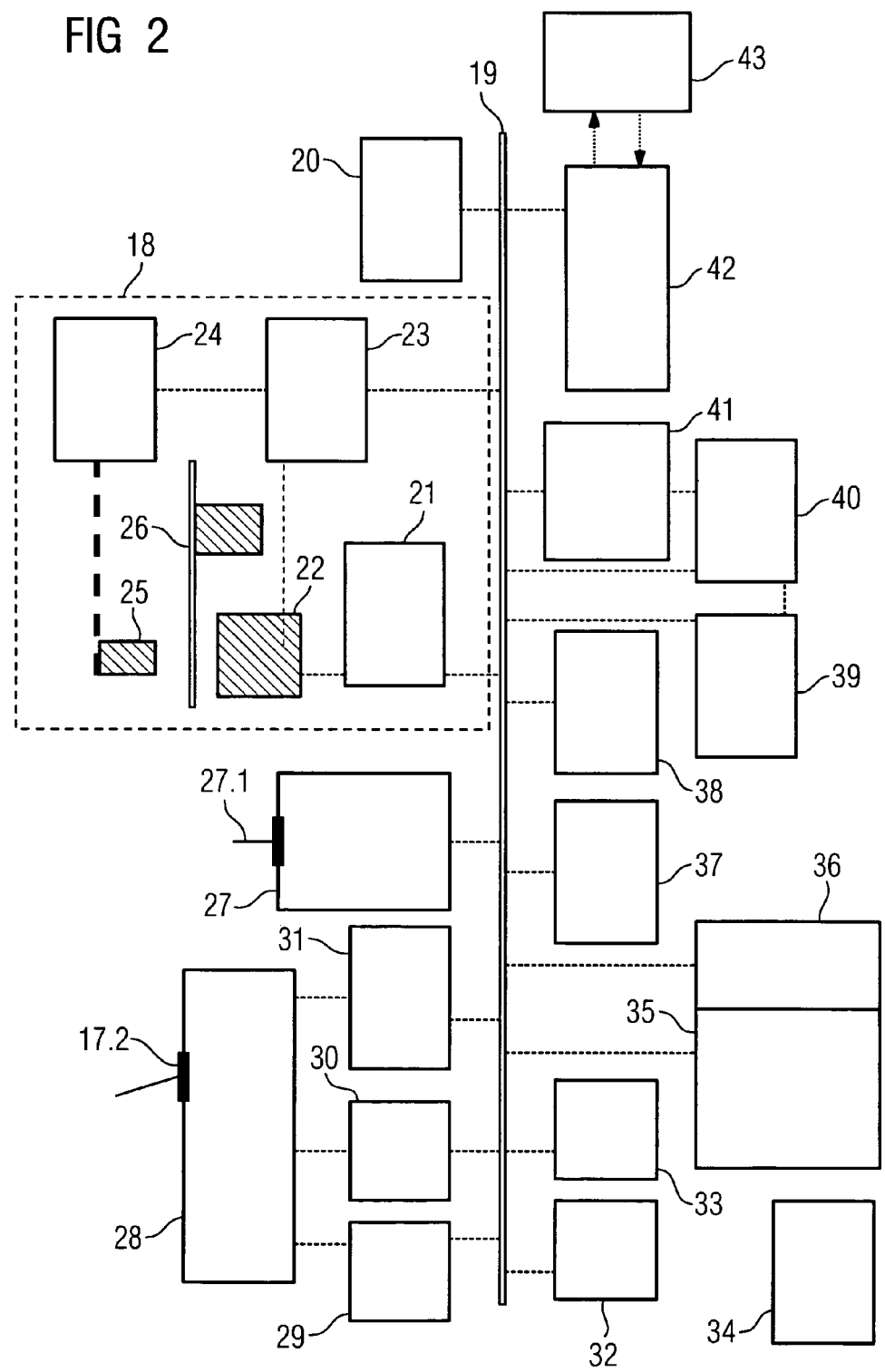

MEDICAL CATHETER AND SYSTEM FOR INSERTING A CATHETER INTO A VESSEL

CROSS REFERENCE TO RELATED APPLICATIONS

This application claims the benefits of German Patent application No. 10 2005 027 951.1 filed Jun. 16, 2005 and is incorporated by reference herein in its entirety.

FIELD OF THE INVENTION

The invention relates to a medical system for the insertion of a catheter into a vessel, preferably a blood vessel of a patient, with a computer and control unit, a means for creating a transparent general image of the position of the vessel, a catheter, located in the front area, with a reversible inflatable balloon on the outside of which a stent can be arranged for implanting in a vessel, and a locating system for the catheter with position and location sensors that can determine the position and location of the front area of the catheter in the space by position sensors (EMP) fitted thereto.

BACKGROUND OF THE INVENTION

One of the most common causes of death in the world is vascular illnesses, particularly cardiac infarction. This is caused by arteriosclerosis, a disease of the coronary vessels. Due to deposits of arteriosclerotic plaque "blockage" of coronary vessels occurs. If a coronary angiography indicates stenosis of the coronary vessels, that causes angina pectoris, that restricts functional capacity and/or threatens a patient, then, at present, a decision is made depending on the features of the case as to whether a bypass operation or a balloon dilatation (Percutaneous Transluminal Coronary Angioplasty=PTCA) is to be performed. In the majority of cases these days a PTCA is carried out. To do this, the narrow parts of the coronary vessels are dilated using a "balloon catheter". A saline solution with 8-15 ATM is forced into the balloon for this balloon dilatation. So that the narrowed vessels do not return to their original condition after the dilatation, a stent has, since the nineties, been inserted into the expanded section of the vessel. A description of a stent is, for example, given in documents DE 299 24 228 A1, DE 200 09 204 A1 and EP 08 78 174 A1.

Up to now, the diagnosis and therapy of the stenosis described above required several process steps. Most frequently, the diagnosis of the stenosis is performed using coronary angiography using a contrast medium under x-ray control. To do this, a catheter is inserted into the coronary vessel and the contrast medium is injected into the coronary vessel. The catheter is then removed. The disadvantage of this method is that only the diameter of the vessel that can be used by the blood flow, i.e. the narrow part, is shown as a silhouette. An assessment regarding deposits, such as thickness or inflammatory processes, is therefore not possible. The advantage of this solution is in the good image quality of the displayed stenosis.

This is followed by insertion of a balloon catheter under x-ray control to expand the stenosis. The catheter must then be withdrawn again.

This is followed by the insertion again of a catheter to position the stent. After the stent has been positioned, the catheter is again removed. The disadvantage of this method is in the relatively poor visibility of the stent in the x-ray image.

A new image-related method is already in use in some clinics. In this case, an intravascular ultrasound catheter (IVUS) is inserted into the coronary vessels and then withdrawn again from the vessel ("pullback"). This method is, for example, described in publication DE 198 27 460 A1. This catheter provides ultrasound images or profiles of the coronary vessels. Usually, the vessel wall is shown in a 360° cross-section. This method provides important medical information regarding deposits and also an adequate image of the stent. The disadvantage of this method is in the limited resolution of the ultrasound images and that an additional catheter has to be inserted into the coronary vessels.

The disadvantage described above should be avoided with a combination catheter as described in international patent application WO 02/07601, but these images suffer from the relatively poor resolution of the ultrasound method. Various clinical studies failed to determine an improved diagnostic method compared with angiography that would justify the higher price for this solution.

A different solution is described in the not previously published patent application with file reference DE 10 2004 001 498.1. This describes a catheter for insertion into a vessel, comprising a reversible inflatable balloon provided in the area of the catheter point on the outside of which a stent for implanting in the vessel is arranged, and at least one imaging device provided in the area of the catheter tip for optical coherence tomography, that is arranged or designed in such a way that an image can be taken of the vessel area in which the balloon is positioned.

In a further not previously published patent application with file reference DE 103 43 808.4, a medical investigation system and/or treatment system is described that combines the OCT and IVUS imaging methods. This is a combination of two imaging methods that superimpose and display the 2D images. Finally, the likewise not previously published patent application with file reference DE 103 54 496.8 also describes a medical investigation and/or treatment system that combines the OCT and IVUS imaging methods and, additionally, provides a position sensor. In this way, 3D images can be created using two-dimensional imaging methods and position and location information.

Reference is also made to publications U.S. Pat. No. 6,233,476 (Medical Positioning System, Strommer et al.) US 2001/0031919 (Medical Imaging Navigation System, Strommer et al.), US 2002/0049375 (Method and Apparatus for Real Time Quantitative Three-Dimensional Image Reconstruction of a Moving Organ and Intra-body Navigation, Strommer et al.). Document 2002/0049375 represents an improvement to U.S. Pat. No. 6,233,476 and US 2001/003191. The device described there shows the spatial position location of a medical catheter by using magnetic fields, partly in combination with an IVUS sensor. The displayed depth area of the vessels is somewhat limited with these solutions. The stressful insertion of a new catheter is necessary to introduce a stent and again there is some uncertainty in the positioning of the stent.

SUMMARY OF THE INVENTION

The object of the invention is therefore to find a medical system for introducing a catheter into a vessel, that with minimum stress to the patient enables a sound diagnosis of a stenosis, thus permitting a good assessment of the vessel wall and at the same time dilatation of the stenosis and positioning of a stent.

The object is achieved by the features of the independent claims. Advantageous developments of the invention are the object of subclaims. The inventor has found that it is possible to describe a suitable combined medical system for inserting a catheter into a vessel that on the one hand provides a three-dimensional image with reference to a previously created general image when advancing the catheter into a vessel, and is thus best suited for an optimum diagnosis, and on the other hand enables the direct placing of a stent in the same work operation with a preceding balloon dilatation in a diagnosed stenosis without having to insert a new catheter.

For this purpose, a catheter with a periphery is proposed that has both OCT and IVUS sensors for image display and can combine correct image position information by means of electromagnetic locating and positioning sensors in the catheter, so that from a number of 2D images from different sources 3D images for making a diagnosis can be created, that can also be combined with a general image. At the same time, this catheter in accordance with the invention has a balloon for dilatation of the vessel and a holder for a stent that can be placed in the same work operation.

A typical sequence of the procedure with a system in accordance with the invention could be as follows.

Insertion of the catheter under x-ray control, with a contrast medium as necessary. Creation of a transparent angiographic general image, creation of a 3D image from OCT and IVUS data by superimposing (segmenting, registering, fusing) and navigating the catheter to the target position on the basis of the images obtained.

The above steps can partly be performed in parallel and automatically without user interaction.

When the required target position is reached, a flushing liquid is injected into the area of the OCT sensor to improve the "view" of the OCT laser and the stenosis is examined using the combined OCT and IVUS methods in 2D or 3D with a high resolution. The stent is positioned and initially fixed by inflating the balloon. The position and location of the stent are then checked using the combined OCT and IVUS methods. The stent can now be finally fixed in place by inflating the balloon at higher pressure, followed by a check of the stent position and withdrawal of the catheter.

Furthermore, the OCT-IVUS-EMP-STENT method described above can have various types of catheter.

It can thus be advantageous to use a known insertion technique by means of a guide wire or guide catheter.

Furthermore, it can be fitted with a known facility for magnetic guidance of the catheter, for example using a permanent magnet, or alternatively by using a solution involving electromagnets at the tip of the catheter or on the catheter. Coils can also be fitted in the catheter as receiving antennas that could also be provided with iron cores, so that with a suitable dimensioning of these coils the unit can be used as a receiving antenna or electromagnet as required. If these coils are controlled as electromagnets, magnetic navigation and control is then possible.

So that changes in the magnetic field caused by the navigation magnets do not result in spurious measuring results of the magnetic locating system, consisting of a transmitter and receiver, the magnetic flux distribution characteristics can be recorded using suitable measuring means and stored after the system is installed. These stored flux distribution characteristics can then be used in the reconstruction of the magnetic location vectras, to avoid measuring errors during location.

The electromagnetic transmitter, or alternatively, the electromagnetic receiver can be housed in the catheter. The relevant electromagnetic receiver or transmitter can conversely be fitted outside the body, whereby advantageously at least one transmitter radiating in the x, y, z direction can be allocated to a receiver or, vice versa, a receiver with an x, y, z direction of reception can be allocated to a transmitter, in order to enable a sound position location in the space. It is, however, also sufficient to combine two directions of transmission in one receiver or, vice versa, if the relationship between the angles of the transmitter devices is known and cannot be changed. If the number of transmitter/receiver units in the space is increased, the position location accuracy increases and, of course, also the computing expense. Methods for electromagnetic position location are known to the person skilled in the art, for example from documents US 2002/0049375, EP 09 93 804 A1 and U.S. Pat. No. 4,054,881.

It is pointed out that nanotechnology can also be used to increase miniaturization. Furthermore, the method in accordance with the invention is not limited to coronary vessels, but can be used for all cavities and vessels in the bodies of humans or animals.

In accordance with the invention, the image information of the IVUS-OCT-EMP-STENT catheter obtained can be correlated with measured position and location information, including with other, preferably 3D, medical images, and combined or superimposed. Such transparent 3D x-ray images can be reconstructed using C-arch devices. Other tomographic methods are also of course suitable for this purpose.

If a calibration is to be carried out, the catheter can be imaged at least once by at least two x-ray projections in the space (x, y, z) and the position in the space determined at least once by the magnetic position locating system (x', y', z'). Both positions are then calibrated against each other by a transformation. It is advantageous if the calibration is not carried out until after installation in the clinic. The accuracy of the calibration can be increased by using a body simulation and calibrating at several points.

To register or superimpose image data of the patient with position data, it is necessary to transfer the spatial coordinates of both objects to a common system of coordinates. Movements of the patient on the examination table can, for example as described in document U.S. Pat. No. 6,233,476, be determined by means of a magnetic ancillary sensor. As an alternative, it is proposed to record the position of the patient using an optical camera or infrared camera and to determine patient movements or displacements using computational methods of pattern recognition and to make corrections in the image processing unit. As an additional possibility, the patient can also be scanned using a laser beam and position displacement determined and corrected.

Furthermore, a functional unit for the removal of movement artifacts, caused by breathing, can be integrated into the system in accordance with the invention. Documents US 2001/0031919 A1 and US 2002/0049375 A1 describe solutions for the removal of the movement artifacts caused by the movement of the heart and of blood vessels. The breathing artifacts can be removed by a breast band that determines the breathing amplitude and frequency using suitable sensors and initiates corrective measures in the image processing unit that computes out the movement artifacts from the image information.

Alternatively, the amplitude and frequency can be calculated from the envelope curve of the ECG signal and applied to the correction unit of the image processing unit. Additionally, the pulsing of the vessels can be used to increase the accuracy when determining the vessel diameter, by evaluating the ECG or the blood pressure curve.

In a particularly preferred embodiment of the system in accordance with the invention, any coils that are present can be arranged orthogonally relative to each other for position determination. It is, however, also possible to arrange them at other angles, e.g. 60 degrees to obtain better miniaturization and ease the introduction of the catheter. It is, of course, necessary to choose angles that are spatially independent of each other so that the position and location sensors can clearly define the position of the catheter. Any deviation from the orthogonal arrangement can be corrected by suitable computing algorithms in the image processing unit.

It is additionally proposed to cyclically operate and evaluate the transmitting coils in certain time intervals with different frequencies, in order to increase the accuracy of the position locating.

Furthermore, the functional units and the signal lead can be provided with devices and measures that shield the physiological signals, the image signals and signal processing and preparation from the magnetic fields of the transmitting antennas.

The connections for the physiological sensors and the catheter can advantageously be decoupled from any power supplies by electrical isolation, in order not to endanger the patient. Optical decoupling is particularly advantageous in this case.

The IVUS sensor can either be designed to be similar to the rotating ultrasound sensor described in document U.S. Pat. No. 6,233,476 or be a fixed ultrasound sensor with omnidirectional radiation and reception. For this purpose, several small ultrasound sensors can be arranged in a ring in the catheter tip that can be cyclically scanned by a multiplexer.

To avoid having too many cable connections to the patient and enable as much free access to the patient as possible, it is proposed to have a wireless data link between the catheter and the associated computer unit as an alternative to cable connections, for example a Bluetooth transmitter/receiving unit can be used.

As an alternative, for position determination of the catheter it is also proposed to additionally use the IVUS ultrasound unit in the catheter as a position transmitter and to locate the position by means of at least one ultrasound receiving unit arranged in the space, capable of receiving in the x, y, z directions.

To improve the accuracy of the position data determined by a magnetic sensor and the vessel pattern determined in this-way, a mathematical envelope curve computation can be used. This takes account of the fact that the catheter can necessarily strike the boundary surfaces of the vessel when inserting, advancing or withdrawing. A number of limit points are generated in this way, the coordinates of which can be determined by the position sensors. A one-dimensional line in a three-dimensional space can then be regarded as the center line of the vessel, that can be calculated using the ascertained limit points and described by a polynomic equation. In a similar manner, the envelope curve of the vessel can be determined from the limit points. A similar procedure to reconstruct the center line of the vessel is described in document U.S. Pat. No. 6,546,271. In addition to the method described in U.S. Pat. No. 6,546,271, to improve the accuracy of the envelope curves approximation the possible minimum and maximum vessel diameters, e.g. 2 mm-9 mm for a coronary vessel, can be estimated for the object under consideration, or the diameter can be estimated from a two-dimensional x-ray angiographic image, or three-dimensional tomographic image. For this method it is, furthermore, proposed that the stiffness and bearing capacity of the catheter be designed so that the space sensors can strike the outer vessel wall as frequently as possible. This can, for example, be achieved in that the catheter sections in the longitudinal direction are designed with different thickness, stiffness and bearing capacity.

Additionally, the catheter can be provided with a coating, e.g. silicone or other hydrophilic coating that facilitates sliding over a guide wire.

Furthermore, a calibration unit can be used that stores the static and dynamic magnetic field states in the various functional stages of the device, e.g. by movement of the C-arch, and uses it to evaluate the signal and calculate the correction for image processing.

In accordance with these embodiments, the inventor proposes to improve a known medical system for the insertion of a catheter into a vessel, preferably a blood vessel of a patient, having at least one computer and control unit, a means for creating a transparent general image of the position of the vessel, a catheter with a reversible inflatable balloon located in the front area on the outside of which a stent for implantation within the vessel can be arranged, and a position locating system for the catheter with position and location sensors that can determine the position and location of the front area of the catheter in the space by means of the position sensors (EMP) mounted thereon, so that the system in the front area is fitted on the catheter end with at least one OCT (optical coherence tomography) imaging sensor for the close-up area with at least one IVUS (Intravascular Ultrasound) image sensor at the catheter end for the remote area, and with the computer and control unit being fitted with image processing and image display functions for the image sensors.

The medical system described above can preferably have further features, mentioned in the following, for example a program means for combining OCT and IVUS image information can additionally be provided, that, of course as with the other program means described later, can be implemented on the computer unit of the system.

Furthermore, a program means for combining image information from the catheter and the position and location information of the catheter can be present, to provide a three-dimensional display of the environment of the catheter.

Furthermore, a program means for combining image information from the catheter and the transparent general image can also be present.

Advantageously, all OCT sensors can be arranged before or after the stent, viewed in the longitudinal direction of the catheter. An arrangement before the stent is advantageous in that when the catheter is being advanced the area in which the stent is actually located is always already known. The same also applies for the IVUS image sensors and the EMP sensors.

Additionally, the catheter can have x-ray markers in the front area that facilitate the display in the x-ray image or CT and also improve the definition of the orientation of the catheter.

The balloon can also be at least partially surrounded by the stent, in order to place it by inflating the balloon.

Furthermore, a calibration device can be provided for the OCT system that continuously compensates for the change in length of the optical path that is associated with a longitudinal movement of the catheter.

Equally, an automatic push/pull device can be provided for the catheter, with the aid of which the movement of the catheter can be computer controlled.

Furthermore, an ECG device can be connected or integrated, with program means providing for the synchronizing of all image and position data with preselected heart phases. In this way, the acuteness of the movements can be eliminated even with a moving heart.

The OCT imaging sensor can be connected to a rotating optical fiber running in the inside of the catheter to take 360° annular images and include a radiation-transparent window, arranged on the side of the catheter sleeve by means of which the radiation can be coupled and decoupled.

The catheter can also have a rotating ultrasound head running in the inside of the catheter to take 360° annular images and an ultrasound-transparent window arranged on the side of the catheter sleeve by means of which the ultrasound can be coupled and decoupled.

Alternatively, the catheter can have an ultrasound head for radiating and receiving ultrasound over an angle of 360° around the circumference of the catheter and an ultrasound-transparent window arranged on the side of the catheter sleeve by means of which the ultrasound can be coupled and decoupled.

An opening to output a fluid, particularly a flushing fluid or a contrast medium, can be provided, preferably adjacent to at least one window.

To move the catheter, a guide wire or an outer guide catheter can be provided, or an element to generate a magnetic field can be provided in the front area to guide the catheter by means of an external magnetic field.

Furthermore, several, preferably three, position sensors for ascertaining the position and/or orientation of the catheter can be provided, with the position sensors having transmission coils arranged in a solid angle, preferably orthogonally, relative to each other, that interact with fixed receiver coils, or the position sensors can also have receiver coils that interact with fixed transmission coils.

The means for creating a transparent general image can, for example, be a C-arch device, preferably with a tomographic evaluation unit, or an x-ray CT device, a nuclear magnetic resonance tomography (NMR) device or a positron emission tomography (PET) device.

The invention is described in more detail in the following using a preferred embodiment and with the aid of illustrations, with only those features necessary for an understanding of the invention being shown. The following reference characters are used: 1: catheter; 2: front area of catheter; 3: rounded catheter tip; 4: magnetic sensors in the x, y, z direction; 5: balloon; 6: stent; 7: ultrasound window; 8: IUS sensor; 9: OTC sensor; 10: OCT window; 11: ultrasound signal lead; 12: OCT signal lead; 13: catheter sleeve; 14: lumen for OCT and IVUS supply lines; 15: signal lead of the EMP sensor; 16: external position sensors or position receivers; 17.1: catheter-end signal interface; 17.2: computer-end signal interface; 18: C-arch device; 19: common databus; 20: image data memory; 21: preprocessing unit for x-ray imager; 22: x-ray detector; 23: system controller; 24: high voltage generator; 25: radiation source; 26: patient couch; 27: physiological signal processing; 27.1: connection to physiological sensors; 28: interface for OCT, IVUS and EMP; 29: preprocessing unit for OCT; 30: preprocessing unit for IVUS; 31: preprocessing unit for EMP; 32: image processing unit for OCT; 33: image processing unit for IVUS; 34: voltage supply; 35: display unit for OCT, IVUS, EMP images and x-ray images; 36: user I/O unit; 37: image processing unit for EMP; 38: image processing unit for x-ray images; 39: calibration unit; 40 image correction unit; 41: image fusion and reconstruction unit; 42: DICOM interface for patient data and image data; 43: further DICOM units; 44: computer and control unit.

BRIEF DESCRIPTION OF THE DRAWINGS

FIG. 1: Catheter in accordance with the invention with combined OCT/IVUS and EMP sensors and stent with dilatation balloon; and FIG. 2: Schematic general view of the periphery of the catheter from FIG. 1.

DETAILED DESCRIPTION OF THE INVENTION

FIG. 1 shows a catheter in accordance with the invention with combined OCT/IVUS and EMP sensors and a stent with a dilatation balloon, whereas FIG. 2 shows a schematic general view of the periphery of this catheter. Both together correspond to the medical system in accordance with the invention, with the necessary and optional program means being shown only as functional units.

FIG. 1 shows the catheter 1 as a schematic longitudinal section. The catheter 1 consists, starting from the front, of a rounded catheter tip 3 behind which is arranged the magnetic sensors 4 for determining the position of the catheter. This is followed by an inflatable balloon 5 that can be inflated at the required point of the vessel by liquid or gas through a supply line. The fluid supply line to this balloon, which of course is present, is omitted for reasons of clarity. It is, however, pointed out that the balloon 5 can also be inflated by other means, for example by a mechanical spreader, without departing from the scope of the invention.

A premounted stent 6 is arranged around the balloon, which when the balloon is expanded is at the same time implanted in the stenosis of the vessel being treated. Connected to the balloon and stent area is an IVUS sensor 8 that is surrounded by an ultrasound-transparent window 7, so that ultrasound waves generated in the IVUS sensor 8 can pass unhindered through this window and at the same time the reflected ultrasound waves can be recorded, in order to create an image of the environment.

Next is the OCT sensor 9 that is also surrounded by an OCT viewing window 10 that is transparent with respect to the particular laser frequency used and thus can scan the close-up area by means of an optical Korenz tomography procedure. The front area of the catheter 1, in which the sensors, the balloon and the premounted stent are located, are regarded as the front area 2. It is pointed out that this arrangement of the various sensors can differ depending on the particular requirements, without departing from the scope of the invention. For example, it can be advantageous to position the ultrasound sensor in the rounded catheter tip because in this way not only is radiation in the radial direction possible but also radiation, and thus also scanning, in the forwards direction, so that the area into which the catheter is moving can be scanned to provide an advance view. Because only the relationship between the position of the EMP sensors and the actual catheter need to be known for position location of the catheter and more precisely the front area of the catheter, it is possible to also position the magnetic sensors further back without losing position or location information. However, the disadvantage of this is that the supply leads for the IVUS sensors and OCT sensors must then pass through the area of the EMP sensors. As an alternative it is also possible to provide for the OCT sensor or IVUS sensor, or both, to be able to be moved in the area of the stent and balloon. In this case, it is of course necessary to know the shift in the position for the 3D image generation.

Next connected to front area 2 is the actual flexible catheter with the catheter sleeve 13, that must be made of physiologically compatible material and must also have good sliding properties. The lumen 14 in which the ultrasound signal leads 11 and the OCT signal leads 12 and, if necessary, also the driveshafts for the OCT sensor and the IVUS sensor are mounted, is located within the catheter sleeve. In this regard, it is pointed out that if the IVUS sensor is also of rotating design, a common driveshaft for both sensors is possible.

In the variant of the catheter shown here, the signal leads 15 to the EMP sensors are arranged between the catheter sleeve 13 and the lumen 14 in which the other sensors signal leads and the driveshaft are arranged.

A signal interface 17.1 is located at the end of the catheter 1 which provides the connection to the computer and control unit 44 via a signal interface 17.2 likewise arranged there. It is pointed out that the data link between the computer and control unit 44 and the catheter need not necessarily be via fixed data lines, but instead can also be a wireless connection, which substantially simplifies the handling of the catheter. For example, a Bluetooth connection or a wireless LAN connection can be used as the wireless connection. It is also pointed out in this respect that the computer and control unit 44 need not necessarily be a single computer system, but instead can be decentralized individual processes that interact with each other by appropriate programming and data links.

The functional construction of the computer and control unit 44 in conjunction with a C-arch device 18 is shown in FIG. 2. The C-arch device consists functionally of a patient couch 26 and a radiation source 25 arranged on a C-arch and swiveling with the C-arch and an x-ray detector 22 arranged opposite, on the other end of the C-arch (not illustrated). Also shown here is the high-voltage supply 24 for the radiation source, that also operates the x-ray detector 22 via a system controller 23. The x-ray detector 22 has a connection to a preprocessing unit in which the transparent general images are generated in the form of x-ray projection images, fluoroscopic images or also in the form of tomographic-reconstructed 3D images. Both the system controller 23 and the preprocessing unit 21 are connected to a common databus 19.

A physiological signal processing unit 27 is also shown in which, for example, ECG, pulse, respiration and blood-pressure information can be processed.

Finally, preprocessing units 29, 30 and 31 are shown, that are responsible for image preprocessing of the OCT, IVUS and EMP signals. All three units are connected to the interface unit 28 that in turn is connected via the interface signal 17.2 to the catheter (not illustrated). The information from the preprocessing units 29, 30 and 31 is also made available on the databus 19. Via this databus 19, the image processing units also connected to it can be used for the OCT information 32, the IVUS information 33, the EMP information 37, and also for x-ray images 38.

Furthermore, a calibration unit 39, that carries out the relevant calibrations in the created images and passes these to an image corrector unit 40, is also connected to the databus 19. The calibrated image data is combined, positioned-corrected, via an image fusion and reconstruction unit 41 and can be output in the required form through the display unit 35 with a connected I/O unit 36. The power supply 34, whose individual connections to the functional units are not explicitly indicated, is also shown. The images obtained can be permanently stored in an image data memory 20 connected to the databus 19, or can also be passed on via a DICOM interface 42 to other DICOM units 43 in the generally known DICOM standard.

It is pointed out that the functional units shown here are realized essentially by program means that are operated on one or more interconnected computer units.

On the basis of the combined information between the general images, obtained by external units, and the image and position sensors in the catheter, it is now possible to obtain a very precise representation of a vessel of a patient that is optimized for diagnostic purposes and thus in the same work operation, in which the structures of the vessel have been rendered visible, to also perform the therapeutic task at the same time, i.e. the placing of a stent preceded by vessel dilatation. This combined procedure enables diagnosis and therapy to be performed that is very gentle for the patient and that furthermore is designed for the optimum economic efficiency due to the short time sequences of the processes.

It is clear that the aforementioned features of the invention can be used not only in the particular combinations given but also in other combinations or on their own, without departing from the scope of the invention.

Overall, the invention shows a combination of OCT and IVUS sensors with simultaneous position and location determination that enables a three-dimensional representation of the environment of the vessel to be created from the two-dimensional image information of the OCT and IVUS sensors in conjunction with position and location determination and knowledge of the position relationship in the sensors, that has a high-resolution close-up area and a sufficiently fine resolution in the remote area, with it being possible to additionally combine this representation with two-or-three-dimensional transparent general images. This enables an optimum vessel diagnosis to be carried out, whereby a balloon dilatation followed by placing of a stent at pathologically diagnosed positions can be realized in one work operation and without additional reinsertion of a catheter.

The invention claimed is:

1. A medical system for inserting a catheter into a blood vessel of a patient, comprising:
    a device for creating a transparent image of the position of the blood vessel in the patient;
    a catheter having a front portion, an inside portion and an outside portion;
    a reversible inflatable balloon arranged at the front portion of the catheter;
    a stent arranged to partially surround the balloon for implanting in the blood vessel;
    an OCT (optical coherence tomography) imaging sensor arranged at the front portion of the catheter to generate image signals in a radial direction and an IVUS (intravascular ultrasound) imaging sensor arranged at a tip of the catheter to generate image signals in a longitudinal direction in advance of a path of travel of the catheter;
    a catheter position locating system having position and location sensors that can determine the position and location of the front portion of the catheter in space, said position and location sensors including transmission coils which are respectively arranged in a solid angle that is orthogonal with respect to each other, said position and location sensors being arranged in the area of the stent and the balloon of the catheter; and
    a computer and control unit for processing and display of the image sensor signals;
    wherein the position sensors and the IVUS sensors and the OCT sensors are arranged so that they can be moved in the longitudinal direction of the catheter.

2. The medical system as claimed in claim 1, wherein software combines the OCT and IVUS image information.

3. The medical system as claimed in claim 2, wherein a three-dimensional display of the environment of the catheter is provided via the combination of image information from the catheter and position and location information of the catheter.

4. The medical system as claimed in claim 3, wherein the combination of image information from the catheter and the transparent general image are performed via software.

5. The medical system as claimed in claim 4, wherein the OCT image sensors, IVUS image sensors, or the position sensors are arranged before or after the stent when viewed in the longitudinal direction of the catheter.

6. The medical system as claimed in claim 5, wherein the catheter has x-ray markers in the front area of the catheter.

7. The medical system as claimed in claim 6, wherein the OCT comprises a calibration device that continuously compensates for a change in length of the optical path associated with a longitudinal movement of the catheter.

8. The medical system as claimed in claim 7, further comprising an ECG device and software for synchronizing all image and position data with a plurality of preselected heart phases.

9. The medical system as claimed in claim 8, wherein the OCT imaging sensor is connected to a rotating optical fiber conductor arranged inside the catheter to take 360° annular images and has a radiation-transparent window at the side of the catheter sleeve wherein a light beam can be coupled and decoupled and an opening for the output of a flushing fluid or a contrast medium is provided adjacent to the window.

10. The medical system as claimed in claim 9, wherein the catheter has a rotating ultrasound head arranged inside the catheter to take 360° annular images and an ultrasound transparent window arranged on the side of the catheter sleeve, wherein the ultrasound can be coupled and decoupled.

11. The medical system as claimed in claim 10, wherein the catheter has an ultrasound head for emitting and for receiving ultrasound over an angle of 360° around the circumference of the catheter and an ultrasound-transparent window arranged on the side of the catheter sleeve wherein the ultrasound can be coupled and decoupled and an opening for the output of a flushing fluid or a contrast medium is provided adjacent to the window.

12. The medical system as claimed in claim 11, wherein a guide wire or an outer guide catheter is provided for moving the catheter.

13. The medical system as claimed in claim 12, further comprising an automatic push/pull device for adjustment of the catheter.

14. The medical system as claimed in claim 13, wherein:
an element for creating a magnetic field to guide the catheter via an external magnetic field is arranged in the front area of the catheter, and
a plurality of position sensors provided to ascertain the position and orientation of the catheter where the position sensors have transmitter coils arranged orthogonally, and interact with fixed receiver coils.

15. The medical system as claimed in claim 14, wherein the transparent general image is a created by a device selected from the group consisting of: a C-arch device with a tomographic evaluation unit, an x-ray CT device, a nuclear magnetic resonance tomography (NMR) device, a positron emission tomography (PET) device, and a single photon emission computer tomography (SPECT) device.

16. The medical system as claimed in claim 15, further comprising a signal interface that attached to the catheter that transmits signals to and from the computer and control unit and the catheter.

17. A medical catheter for insertion into a blood vessel of a patient, comprising:
a catheter body having a front portion, a rear portion, an inside portion and an outside portion;
a reversible inflatable balloon arranged at the front portion of the catheter;
a stent arranged over the balloon for implanting in the blood vessel;
an OCT (optical coherence tomography) imaging sensor arranged at the front portion of the catheter to generate image signals in a radial direction and an IVUS (intravascular ultrasound) imaging sensor arranged at a tip of the catheter to generate image signals in a longitudinal direction in advance of a path of travel of the catheter;
a catheter position locating system having position and location sensors that can determine the position and location of the front portion of the catheter in space, said position and location sensors including transmission coils which are respectively arranged in a solid angle that is orthogonal with respect to each other, said position and location sensors being arranged in the area of the stent and the balloon of the catheter; and
a signal interface arranged at the rear portion of the catheter that transmits image signals to a computer and receives signals from a control unit.

\* \* \* \* \*